United States Patent
Gacsalyi et al.

(10) Patent No.: US 8,318,743 B2
(45) Date of Patent: Nov. 27, 2012

(54) MEDICAMENT FOR THE ENHANCEMENT OF COGNITIVE FUNCTION AND NEUROPROTECTION

(75) Inventors: Istvan Gacsalyi, Budapest (HU); Gabor Gigler, Budapest (HU); Marta Agoston, Budapest (HU); Hajnalka Kompagne, Budapest (HU); Szabolcs Kertesz, Fót (HU); Krisztina Moricz, Budapest (HU); Gyoergy Levay, Budapest (HU); Gabor Szenas, Ueroem (HU); László Gabor Harsing, Budapest (HU); Jozsef Barkoczy, Budapest (HU); Gyula Simig, Budapest (HU)

(73) Assignee: Egis Gyogyszergyar Nyilvanosan Mukodo Reszvenytarsasag, Budapest (HU)

( * ) Notice: Subject to any disclaimer, the term of this patent is extended or adjusted under 35 U.S.C. 154(b) by 410 days.

(21) Appl. No.: 12/307,385

(22) PCT Filed: Jul. 3, 2007

(86) PCT No.: PCT/HU2007/000059
§ 371 (c)(1),
(2), (4) Date: Sep. 9, 2009

(87) PCT Pub. No.: WO2008/004013
PCT Pub. Date: Jan. 10, 2008

(65) Prior Publication Data
US 2010/0075975 A1 Mar. 25, 2010

(30) Foreign Application Priority Data
Jul. 3, 2006 (HU) .................................. 0600555

(51) Int. Cl.
*A61K 31/501* (2006.01)
(52) U.S. Cl. .................................. 514/252.03
(58) Field of Classification Search ............... 514/252.03
See application file for complete search history.

(56) References Cited

U.S. PATENT DOCUMENTS

| 7,183,283 B2 | 2/2007 | Barkoczy | 514/252.03 |
| 7,307,168 B2 | 12/2007 | Pongo | 544/282 |
| 2003/0024849 A1 | 2/2003 | Nielsen | 206/531 |

FOREIGN PATENT DOCUMENTS

| WO | WO-9815541 | 4/1998 |
| WO | WO-0117993 | 3/2001 |

OTHER PUBLICATIONS

Khairallah et al.; "Alzheimer's disease: current status of etiopathogenesis and therapeutic strategies"; 2011; Pak J Biol Sci. ;14(4):257-72 PubMed abstract; PMID: 21870628.*
Stix; Alzheimer's: Forestalling the Darkness; Jun. 2010; Scientific American; 50-57.*

* cited by examiner

*Primary Examiner* — Timothy Thomas
(74) *Attorney, Agent, or Firm* — Jonathan Myers; Andrew Wilford

(57) ABSTRACT

The invention relates the use of 4-chloro-5-{2-[4-(6-fluoro-1,2-benz[d]isoxazole-3-yl)piperidin-1-yl]ethyl-amino}-2-methyl-3-(2H)pyridazinone of the Formula (I)

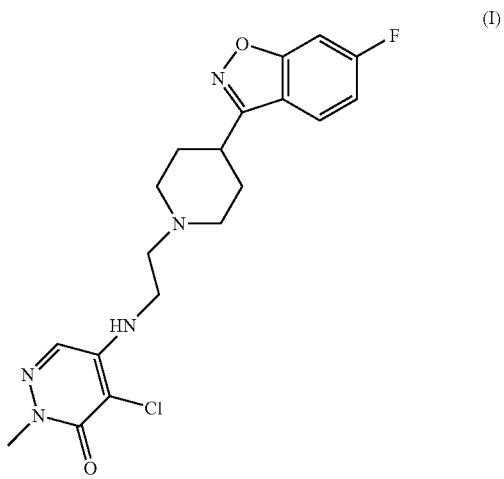

or pharmaceutically acceptable salts thereof for the preparation of medicaments suitable for the improvement of cognitive function or obtaining neuroprotective effect.
The medicaments containing 4-chloro-5-{2-[4-(6-fluoro-1,2-benz[d]isoxazol-3-yl)piperidin-1-yl]ethyl-amino}-2-methyl-3-(2H)pyridazinone of the Formula (I) or therapeutically acceptable salt thereof can be used for the treatment or prevention of neuronal death, mental decline, sclerosis multiplex, Creuzfeld-Jacobs disease, Huntington-syndrome, amyotrophic lateral sclerosis, Parkinson-disease, memory disturbance, loss of memory, amnesia, stroke or for the improvement of memory function or learning ability.

5 Claims, 6 Drawing Sheets

The effect of 4-chloro-5-{2-[4-(6-fluoro-1,2-benz[d]isoxazol-3-yl)piperidin-1-yl]ethyl-amino}-2-methyl-3-(2H) pyridazinone (T) and risperidone (R) in permanent focal ischemia model in the rat 4-chloro-5-{2-[4-(6-fluoro-1,2-benz[d]isoxazol-3-yl)piperidin-1-yl]ethyl-amino}-2-methyl-3-(2H) pyridazinone (T)

The effect of 4-chloro-5-{2-[4-(6-fluoro-1,2-benz[d]isoxazol-3-yl)piperidin-1-yl]ethyl-amino}-2-methyl-3-(2H) pyridazinone (test) and risperidone (risp) in passive avoidance model The effect of 4-chloro-5-{2-[4-(6-fluoro-1,2-benz[d]isoxazol-3-yl)piperidin-1-yl]ethyl-amino}-2-methyl-3-(2H) pyridazinone (test) in scopolamine-induced memory deficiency in the eight-arm maze test The effect of 4-chloro-5-{2-[4-(6-fluoro-1,2-benz[d]isoxazol-3-yl)piperidin-1-yl]ethyl-amino}-2-methyl-3-(2H) pyridazinone in object recognition model (test compound)

*: $p<0.05$ compared to control

MEDICAMENT FOR THE ENHANCEMENT OF COGNITIVE FUNCTION AND NEUROPROTECTION

CROSS REFERENCE TO RELATED APPLICATIONS

This application is the US national phase of PCT application PCT/HU2007/000059, filed 3 Jul. 2007, published 10 Jan. 2008 as WO2008/004013, and claiming the priority of Hungarian patent application P0600555 itself filed 3 Jul. 2006, whose entire disclosures are herewith incorporated by reference.

FIELD OF THE INVENTION

The present invention relates to the use of 4-chloro-5-{2-[4-(6-fluoro-1,2-benz[d]isoxazole-3-yl)piperidine-1-yl]ethyl-amino}-2-methyl-3-(2H)pyridazinone of the Formula (I)

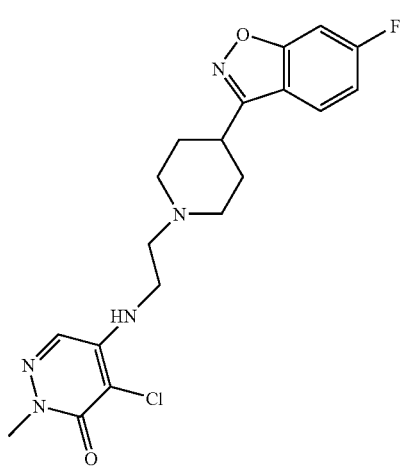

(I)

and pharmaceutically acceptable salts thereof for the preparation of medicaments suitable for the enhancement of cognitive function or having neuroprotective effect and corresponding methods of treatment.

BACKGROUND OF THE INVENTION 4-chloro-5-{2-[4-(6-fluoro-1,2-benz[d]isoxazole-3-yl)piperidine-1-yl]ethyl-amino}-2-methyl-3-(2H)pyridazinone of the Formula (I) and pharmaceutically acceptable salts thereof have been disclosed for the first time in published International Patent Application No. WO 03/010166 and in Hungarian Patent Application No. PO 103063.

It is known from the state of the art that 4-chloro-5-{2-[4-(6-fluoro-1,2-benz[d]isoxazole-3-yl)piperidine-1-yl]ethyl-amino}-2-methyl-3-(2H)pyridazinone of the Formula (I) is a drug candidate having a valuable neuroleptic effect useful in the treatment of psychoses, especially schizophrenia. The expression "neuroleptic effect" is understood according to the state of the art as the alleviating effect of the antipsychotic drug towards the embarrassment, delusions, hallucinations and psychomotoric excitation resulting from psychoses in patient suffering from such disorders.

In recent decades, several diseases have emerged in the of interest of medicinal research, which are associated with neuronal death, chronic neuronal decay, decline of mental capabilities or dementia resulting from the progress of aging.

Such disorders include multiple sclerosis, Creuzfeld-Jacob disease, Huntington's Disease, amyotrophic lateral sclerosis (ALS), Parkinson's Disease, stroke and neuronal death due to acute cerebral or spinal traumas or resulting from the exposure of toxic substances or as a result of ischemia. Characteristic symptoms of the above-mentioned disorders are a decrease of learning capability, loss of memory and in some cases, a decline in mental ability.

According to the state of the art, two types of memory are distinguished. The so-called "short-term memory" characterizes refers to the retention of information for a short interval of time spanning from some minutes to several hours. The expression "long-term memory" refers to the retention of information for the periods ranging from hours to years (Baddley and Warington, J. Verb. Learn. Verb. Behav. 9, 176-179); Wright et al., Science 229, 287-289).

The process of information transfer from short-term memory to long-term memory is referred to as consolidation.

The process of bringing back the information from either short-term or long-term memory is called retention.

Although total amnesia is relatively rare, the incidence of the disorders accompanied by confused memory or memory decline is increasing. Eighteen million people are suffering from Alzheimer's Disease worldwide and a significant increase in the number of patients suffering in this disease is expected in the upcoming years (Fletcher, Mol. Med. Today, 3/10 p. 429-434, 1997).

OBJECTS OF THE INVENTION

On the basis of the above facts, the object of our research was to develop medicaments suitable for the treatment of disorders and diseases associated with confused memory and memory decline, which are not related to psychoses.

The above object is achieved by the present invention.

A further object of the present invention is a process for influencing the cognitive function or providing neuroprotective effect by administering to the patient in need of such treatment 4-chloro-5-{2-[4-(6-fluoro-1,2-benz[d]isoxazol-3-yl)piperidin-1-yl]ethyl-amino}-2-methyl-3-(2H)pyridazinone or a pharmaceutically acceptable acid addition salt thereof in a therapeutically efficient quantity.

SUMMARY OF THE INVENTION

The present invention is based on the surprising recognition that 4-chloro-5-{2-[4-(6-fluoro-1,2-benz[d]isoxazole-3-yl)piperidine-1-yl]ethyl-amino}-2-methyl-3-(2H)pyridazinone of the Formula (I) or a pharmaceutically acceptable salt thereof proved to be effective in the prevention of neuronal death resulting from global cerebral ischemia or in the prevention of neuronal damage due to focal cerebral ischemia in animal model experiments. Furthermore, it was found that the chemically similar risperidone {3-(2-(4-(6-fluoro-1,2-benz[d]isoxazole-3-yl)-1-piperidinyl)-ethyl)-6,7,8,9-tetrahydro-2-methyl-4H-pyrido[1,2-a]pyrimidin-4-one} of the Formula (II)

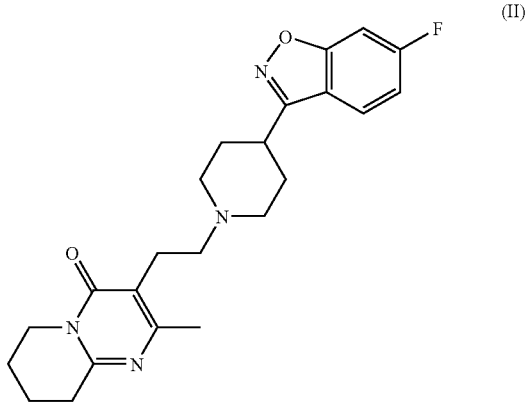

(II)

or other antipsychotic drugs are exempt from such an effect. Therefore, it can be concluded that the above-mentioned neuroprotective effect is unrelated to the known antipsychotic effect of the compound of the Formula (I).

Due to the presently recognized neuroprotective effect, 4-chloro-5-{2-[4-(6-fluoro-1,2-benz[d]isoxazole-3-yl)piperidin-1-yl]ethyl-amino}-2-methyl-3-(2H)pyridazinone of the Formula (I) and pharmaceutically acceptable salts thereof can be used for the improvement of behavioural parameters resulting from neuronal death in multiple sclerosis, motoneuron disease (i.e. amyotrophic lateral sclerosis, ALS), Creutzfeld-Jacob disease, Huntington's Disease and Parkinson's Disease.

Furthermore, during the pharmacological tests carried out with 4-chloro-5-{2-[4-(6-fluoro-1,2-benz[d]isoxazole-3-yl)piperidin-1-yl]ethyl-amino}-2-methyl-3-(2H)pyridazinone of the Formula (I), it was found that the compound is effective in those in vivo animal models which are suited for the detection of enhancement of learning capacity and functional effects associated with memory-improving effects, e.g. passive avoidance behavior model, eight-arm labyrinth model and the so-called object recognition model. The prior art is silent about the enhancing effect on learning capacity and memory improving effects of antipsychotics, e.g. the chemically similar risperidone of the Formula (II).

The surprising neuroprotective and memory-enhancing effect as well as the learning improvement effect of 4-chloro-5-{2-[4-(6-fluoro-1,2-benz[d]isoxazole-3-yl)piperidin-1-yl] ethyl-amino}-2-methyl-3-(2H)pyridazinone described above manifest themselves in individuals not suffering in psychoses. Therefore, the above-mentioned effects are independent of the antipsychotic effect of the compound of the Formula (I) known from the prior art.

DETAILED DESCRIPTION OF THE INVENTION

On the basis of the above-mentioned effects, 4-chloro-5-{2-[4-(6-fluoro-1,2-benz[d]isoxazole-3-yl)piperidine-1-yl] ethyl-amino}-2-methyl-3-(2H)pyridazinone of the Formula (I) and pharmaceutically acceptable salts thereof are suitable for the treatment of diseases and disorders associated with the loss of learning ability, memory disturbances or mental decline, e.g. conditions resulting from acute cerebral or spinal damage, stroke, cerebral spasms, neuronal death following cerebral or spinal traumas. Furthermore, mental decline due to aging the decline in cognitive functions resulting from the effect of toxic substances can also be treated by administering 4-chloro-5-{2-[4-(6-fluoro-1,2-benz[d]isoxazole-3-yl)piperidin-1-yl]ethyl-amino}-2-methyl-3-(2H)pyridazinone of the Formula (I) or a pharmaceutically acceptable salt thereof.

In the present description, under the expression "pharmaceutically acceptable salts" are meant the salts prepared by reacting 4-chloro-5-{2-[4-(6-fluoro-1,2-benz[d]isoxazol-3-yl)piperidin-1-yl]ethyl-amino}-2-methyl-3-(2H)pyridazinone of the Formula (I) with a pharmaceutically acceptable, non-toxic inorganic or organic acid. Such pharmaceutically acceptable salts are salts of the compound of the Formula (I) e.g. with hydrogen chloride, hydrogen bromide, sulfuric acid, phosphoric acid, nitric acid, acetic acid, tartaric acid, maleic acid, fumaric acid, lactic acid, malic acid, citric acid, benzenesulfonic acid, toluenesulfonic acid, methanesulfonic acid etc.

Figure 1:
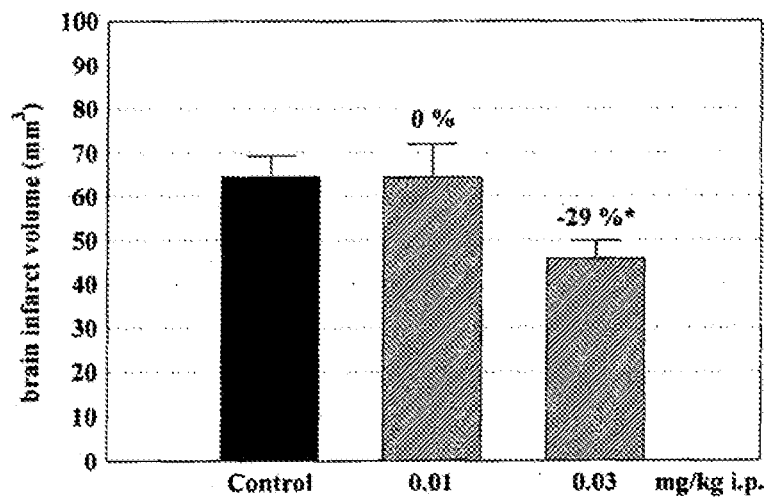
FIG. 1 is a series of bar graphs comparing the effects of i.p. administration to rats with artificially occluded carotid and cerebral arteries, using various doses of 4-chloro-5-{2-[4-(6-fluoro-1,2-benz[d]isoxazole-3-yl)piperidin-1-yl]ethyl-amino}-2-methyl-3-(2H)pyridazinone against a control and using various doses of risperidone against a control on the size of the cerebral infarct resulting from the occlusion of the carotid and cerebral arteries.
Figure 1:
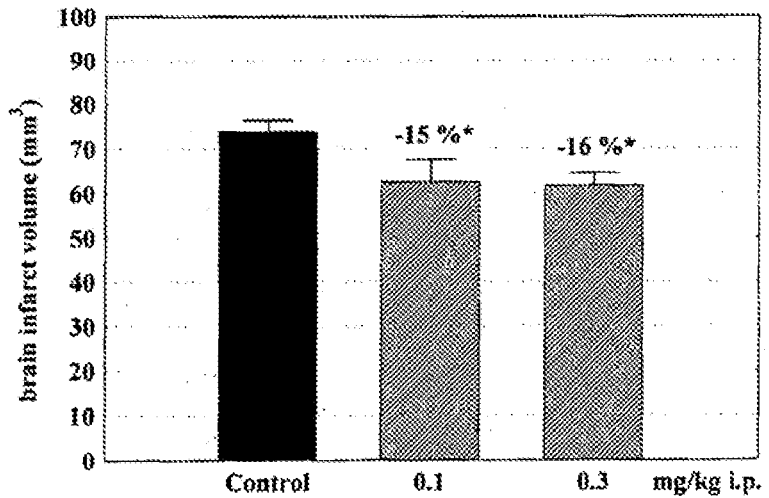
Figure 1:
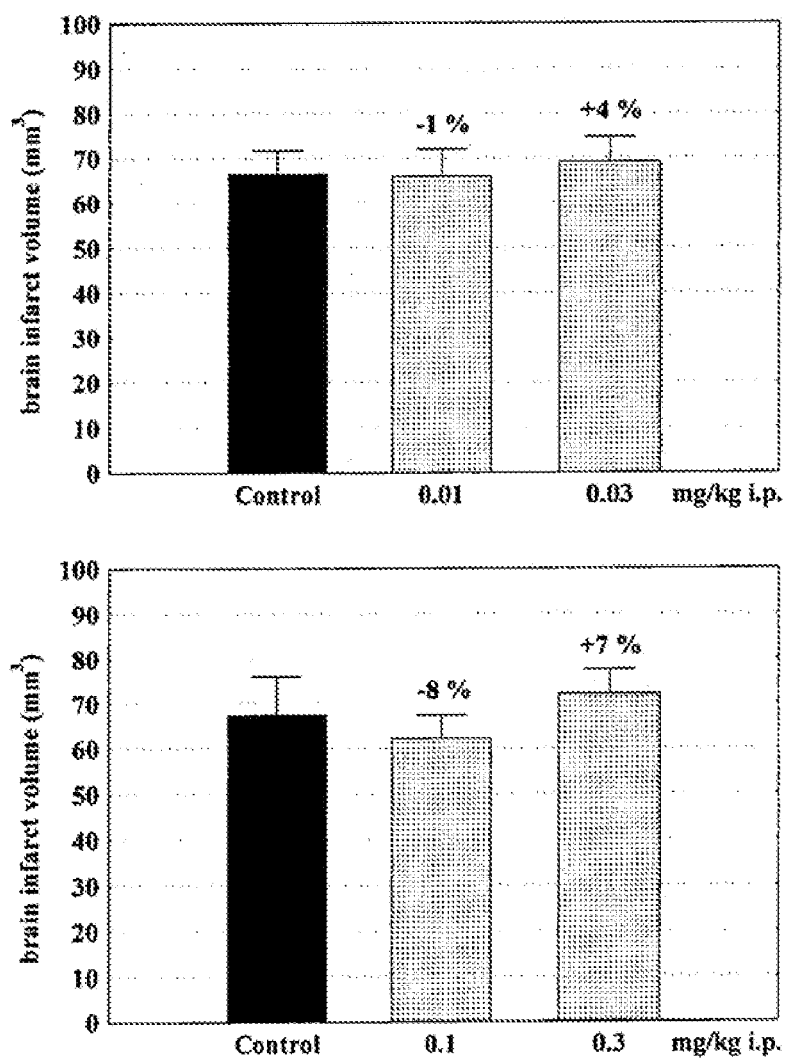

The neuroprotective effect of 4-chloro-5-{2-[4-(6-fluoro-1,2-benz[d]isoxazole-3-yl)piperidin-1-yl]ethyl-amino}-2-methyl-3-(2H)pyridazinone of the Formula (I) was tested in gerbils by global cerebral ischemia model by bilateral occlusion of the carotid artery and in rats by focal cerebral ischemia model via the permanent occlusion of the central cerebral artery. Risperidone[3-(2-(4-(6-fluoro-1,2-benz[d]isoxazole- 3-yl)-1-piperidinyl)ethyl)-6,7,8,9-tetrahydro-2-methyl-4H-pyrido[1,2-a]pyrimidin-4-one] of the Formula (II) was used as reference compound.

The tests in the global cerebral ischemia model were performed in male gerbils weighing 50-80 g. During surgery, the animals were anaesthetized with ether, and the carotid arteries were set free in the paratracheal region by a ventral incision in the central region. The carotid arteries were separated from the vagosympatic nerve-trunk and were occluded for 3 minutes using artery forceps and subsequently released. The body temperature of the animals was checked during surgery and was kept in the normal range using an infrared lamp (37.5±0.5° C.). The test substance 4-chloro-5-{2-[4-(6-fluoro-1,2-benz[d]isoxazole-3-yl)piperidin-1-yl]ethyl-amino}-2-methyl-3-(2H)pyridazinone of the Formula (I) and the reference substance risperidone of the Formula (II) were administered in a dose of 0.1 mg/kg intraperitoneally 45 minutes after surgery.

Four days after surgery, animals were anaesthetised using pentobarbital-Na (60 mg/kg ip., 10 ml/kg) and the brains were perfused with saline thorough the left ventricle. The perfusion was continued for an additional 30 minutes using fixative solution (200 ml/animal). The fixative solution contained 0.1% of glutaraldehyde, 4% of paraformaldehyde and 0.2% of picric acid in 0.1 M phosphate buffer (pH 7.4). After perfusion, the brains were removed from the skulls and were stored in the above-mentioned fixative solution for at least one week at 4° C. in a refrigerator.

The cerebral part containing the dorsal hippocampus has been dissected into 60-μm thick coronal sections using a freezing microtome. The sections were washed four times by shaking for 30 minutes in 0.1 M phosphate buffer (pH 7.4) during which the cerebral sections were floating in the washing solution. Subsequently the cerebral sections were stained using silver impregnation. The staining by the silver impregnation method comprises (a) immersing the sample into a preparatory solution twice for 5 minutes (the preparatory solution comprises aqueous 2% sodium hydroxide and 0.875% ammonium hydroxide solution); (b) immersing the sample into the impregnating solution for 10 minutes (solution of 0.875% ammonium hydroxide and 0.5% silver nitrate in water), (c) washing the sample twice for 2 minutes and finally for one minute in the solution of 0.5% of sodium carbonate and 0.01% ammonium nitrate in aqueous 29.1% ethanol); (d) development for one minute by immersing the section into a development solution (1-1.5% formaldehyde and 0.01% ammonium nitrate in 9.9% ethanol), (e) fixation three times for three minutes each in 0.5% acetic acid solution. The stained cerebral sections were placed into 0.1 M phosphate buffer (pH 7.4) and subsequently chromic gelatine, mounted on slides and dehydrated (dried), treated with xylene for 10 minutes and the cover plates were attached using DPX histological adhesive (Fluka).

The bilateral neuronal damage in the CA1 region of the hippocampus have been evaluated on a six-score scale as follows: 0—no damage observed; 1—0-10% neuronal damage; 2—10-30% neuronal damage; 3—30-50% neuronal damage; 4—50-70% neuronal damage; 5—70-90% neuronal damage; 6—90-100% neuronal damage. The average scores measured in the treated group were expressed in the percentage of the average scores observed in the case of the control animals. The statistical evaluation was carried out by non-parametric Mann-Whitney U-test. The results are summarized in Table 1.

TABLE 1

The effect of 4-chloro-5-{2-[4-(6-fluoro-1,2-benz[d]-isoxazole-3-yl)piperidin-1-yl]ethyl-amino}-2-methyl-3-(2H) pyridazinone of the Formula (I) and risperidone on the hippocampal neuronal damage observed in global ischemia produced by bilateral carotid artery occlusion in gerbils

| Compound | Dose mg/kg ip. | CA 1 lesion | Effect % |
|---|---|---|---|
| Control | — | 5.22 | — |
| 4-chloro-5-{2-[4-(6-fluoro-1,2-benz[d]isoxazol-3-yl)-piperidin-1-yl]ethyl-amino}-2-methyl-3-(2H)pyridazinone [compound of the Formula (1)] | 0.1 | 2.80** | −46 |
| Control | — | 4.75 | — |
| Risperidone [Compound of the Formula (II)] | 0.1 | 4.67 | −2 |

**p < 0.01, vs. control, Mann- Whitney U-test

The above experimental data prove that 4-chloro-5-{2-[4-(6-fluoro-1,2-benz[d]isoxazole-3-yl)piperidin-1-yl]ethyl-amino}-2-methyl-3-(2H)pyridazinone of the Formula (I) significantly decreased the proportion of the neuronal damage in CA1 region of the hippocampus in the dose of 0.1 mg/kg ip., while risperidone of the Formula (II) was ineffective in the same dose.

In the experiments aimed at studying the effect of the compound of the Formula (I) in a focal cerebral ischemic model, the procedure of Brint and coworkers was used (Brint, S. Focal brain ischemia in the rat: methods for reproducible neocortical infarction using tandem occlusion of the distal middle cerebral and ipsilateral common carotid arteries. J. Cereb. Blood Flow Metab. 8: 474-485, 1988).

Male SPRD rats weighing 200 to 220 g were anesthesized with 60 mg/kg i.p. pentobarbital and the distal arm of the central cerebral artery and the carotid artery on the same side were occluded using an electric cauter. The test and reference compounds were administered intraperitoneally 30 minutes after surgery. 48 hours after surgery, rats were anaesthetized again using 120 mg/kg i.p. pentobarbital and the brains were perfused through the left cardiac ventricle with 3 ml of 4-percent 2,3,5-triphenyltetrazolium chloride (TTC) solution. After one hour, the brains were removed and were placed instantly into ice-cooled saline for 1-2 minutes.

Subsequently, the brains were placed into 8% formalin solution one by one. After 24 hours, 1-mm thick coronal sections were made and the area of the damaged brain tissue was determined by a computerized image recording and analysis system. The statistical analysis was carried out by ANOVA and Duncan-test. The results are summarized in Table 2 and FIG. 1.

TABLE 2

The effect of 4-chloro-5-{2-[4-(6-fluoro-1,2-benz[d]isoxazole-
3-yl)-piperidin-1-yl]ethyl-amino}-2-methyl-3-(2H) pyridazinone
and risperidone on permanent focal ischemia in rats

| Compound | Dose mg/kg ip | Dead cerebral volume mm$^3$ ± SE | Effect % | No. Of Cases N |
|---|---|---|---|---|
| Control | — | 64.41 ± 4.80 | — | 8 |
| 4-chloro-5-{2-[4-(6-fluoro-1,2-benz[d]isoxazol-3-yl)piperidin-1-yl]ethyl-amino}-2-methyl-3-(2H)pyridazinone | 0.01 | 64.33 ± 7.66 | 0 | 11 |
|  | 0.03 | 45.70 ± 4.11 | −29 | 11 |
| Control | — | 73.83 ± 2.61 | — | 15 |
| 4-chloro-5-{2-[4-(6-fluoro-1,2-benz[d]isoxazol-3-yl)piperidin-1-yl]ethyl-amino}-2-methyl-3-(2H)pyridazinone | 0.1 | 62.63 ± 4.86* | −15 | 12 |
|  | 0.3 | 61.79 ± 2.69* | −16 | 10 |
| Control | — | 66.37 ± 5.31 | — | 8 |
| Risperidone | 0.01 | 65.91 ± 6.08 | −1 | 8 |
|  | 0.03 | 69.09 ± 5.71 | 4 | 8 |
| Control | — | 67.41 ± 8.72 | — | 8 |
| Risperidone | 0.1 | 62.17 ± 5.17 | −8 | 8 |
|  | 0.3 | 72.07 ± 5.48 | 7 | 8 |

*P < 0.01

On the basis of the results obtained in the focal cerebral ischemic model in rats, it is concluded that 4-chloro-5-{2-[4-(6-fluoro-1,2-benz[d]isoxazole-3-yl)piperidin-1-yl]ethyl-amino}-2-methyl-3-(2H)pyridazinone of the Formula (I) decreased the cerebral infarct size in statistically significant manner if administered in the dose of 0.03 mg/kg i.p., while risperidone of the Formula (II) proved to be ineffective in the same dosage range (0.01-0.3 mg/kg ip.).

In the animal experiments presented above, 4-chloro-5-{2-[4-(6-fluoro-1,2-benz[d]isoxazole-3-yl)piperidin-1-yl]ethyl-amino}-2-methyl-3-(2H)pyridazinone of the Formula (I) prevented the neuronal damage resulting from global cerebral ischemia and the brain tissue damage due to focal cerebral ischemia. These effects of 4-chloro-5-{2-[4-(6-fluoro-1,2-benz[d]isoxazole-3-yl)-piperidin-1-yl]-ethyl-amino}-2-methyl-3-(2H)pyridazinone of the Formula (I) are unexpected, since risperidone of the Formula (II) having similar effect to the known antipsychotic activity of 4-chloro-5-{2-[4-(6-fluoro-1,2-benz[d]isoxazole-3-yl)piperidin-1-yl]-ethyl-amino}-2-methyl-3-(2H)pyridazinone, does not exhibit any neuroprotective effect.

The influence of 4-chloro-5-{2-[4-(6-fluoro-1,2-benz[d]isoxazole-3-yl)piperidin-1-yl]ethyl-amino}-2-methyl-3-(2H)pyridazinone on the learning and memory processes was investigated in rats using the passive avoidance, eight-arm radial maze and object recognition tests.

The passive avoidance tests were carried out in male Wistar rats weighing 200 to 220 g (Charles River, Budapest). The experimental animals were kept in a room having a circadian light-dark periods of 12-12 hours. The light was switched on at 6:00 am. The relative humidity of the room was 60±10%.

The tests were carried out in a so-called step-through type apparatus with five channels which is suitable for testing of passive avoidance learning.

The apparatus comprises two plexiglass boxes of 20×20×16 cm. One of the boxes is clear, the other one is non-transparent, black-painted. There exists a separating wall between the boxes having an opening of 7.5×8 cm. The opening can be opened or closed by a computer-controlled shutter door. The transition of the rat from one box into the other is detected by two parallel photocell rows and the door is automatically shut after the transition of the animal. The floor of the black-painted box consists of stainless steel rods equipped with an electrical circuit suitable for the delivery of an electric shock. There is a 10-W bulb above the door at the light (transparent) side of the apparatus.

The tests were carried out on two subsequent days with a 24-hour time difference.

The first part of the test is the so-called acquisition period, wherein the animal is able to gain specific information characteristic to the situation (upon entry into the dark box, an electric shock is delivered). The second part of the test is the so-called retention period. In this stage, the ability of the animal to remember the information which was collected in the first part is tested (upon entry into the dark part, an electric shock will be delivered, therefore it is less traumatic to stay in the light compartment).

On the first day of the testing (acquisition period), the numbered animals are placed into the clear compartment of the apparatus while the shutter door is closed. After 30 seconds, the door is opened and the animal could freely enter the dark box. At the same time, the clock for the measurement of the transition latency was started. The transition latency is the period of time which elapses between the opening of the shutter door and the transition of the animal from the light compartment into the dark one. When the animal entered the dark box, the clock measuring the latency is stopped. 3 seconds after the entry into the dark compartment, an electric shock of 0.4 mA is delivered for 10 seconds to the animals in the form of a paw shock. Animals belonging to the absolute control groups were not delivered a paw shock. After the electric shock, the animals were immediately removed from the apparatus. A 180-sec period was available for the animals to enter the dark compartment. The role of the absolute control group is to demonstrate that the animal is able to remember the electric shock. This is the essence of acquisition.

During the second-day test (retention) after 24 hours, the animals were placed into the apparatus again. The subsequent part of the procedure was identical to that performed on the first day with the only difference that except for one group, no electric shock was delivered to the animals. Similarly to the first day, 180 sec was provided for the animals to enter the dark box.

During the tests directed to the determination of the effect of 4-chloro-5-{2-[4-(6-fluoro-1,2-benz[d]isoxazole-3-yl)piperidin-1-yl]ethyl-amino}-2-methyl-3-(2H)pyridazinone of the Formula (I), the experimental animals were treated with the test substance and the reference substance or with vehicle (0.4% methylcellulose) on the second day, 60 minutes before placing the animals into the apparatus. The treatment was carried out orally at a dose of 0.005 mg/kg in a volume of 5 ml/kg.

The statistical evaluation was carried out with multiple way variance analysis. The differences between groups were analyzed by Duncan-test.

Figure 2:
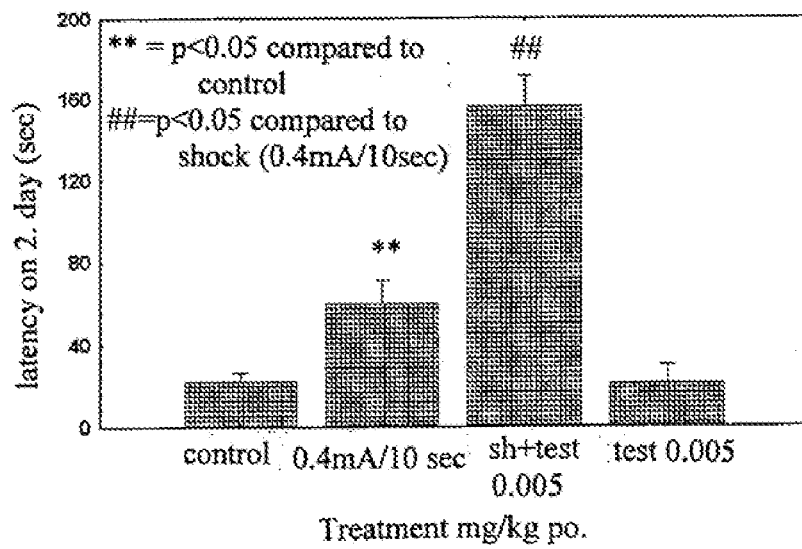
FIG. 2 is a series of bar graphs comparing the effects in rats on learning and memory subjected to the passive avoidance test conducted over a two-day period for determining effects on learning and memory processes, following oral administration of 4-chloro-5-{2-[4-(6-fluoro-1,2-benz[d]isoxazole-3-yl)piperidin-1-yl]ethyl-amino}-2-methyl-3-(2H)pyridazinone at a dose of 0.005 mg/kg against a control and following oral administration of risperidone also at a dose of 0.005 mg/kg against a control.
Figure 2:
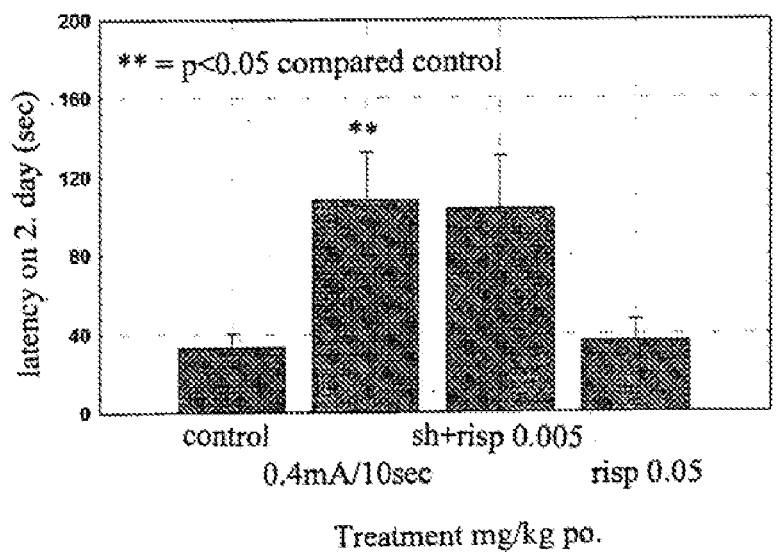
Figure 3:
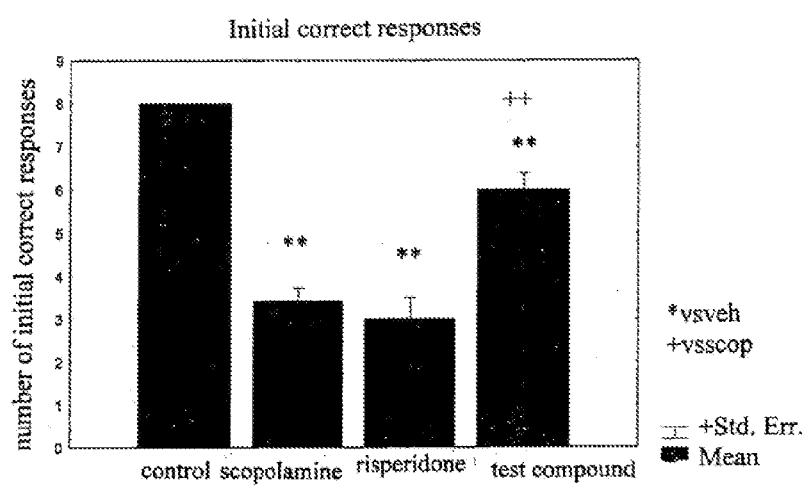
FIG. 3 is a series of bar graphs comparing initial correct responses, working memory errors, and number of total errors in rats subjected to the scopolamine-induced memory deficit test in which rats were administered a vehicle as a negative control, 0.5 mg/kg i.p. scopolamine as a positive control, and either 0.5 mg/kg i.p. scopolamine and 0.01 mg/kg 4-chloro-5-{2-[4-(6-fluoro-1,2-benz[d]isoxazole-3-yl)piperidin-1-yl]ethyl-amino}-2-methyl-3-(2H)pyridazinone or 0.5 mg/kg i.p. scopolamine and 0.01 mg/kg risperidone to determine the effect of each on memory.
Figure 3:
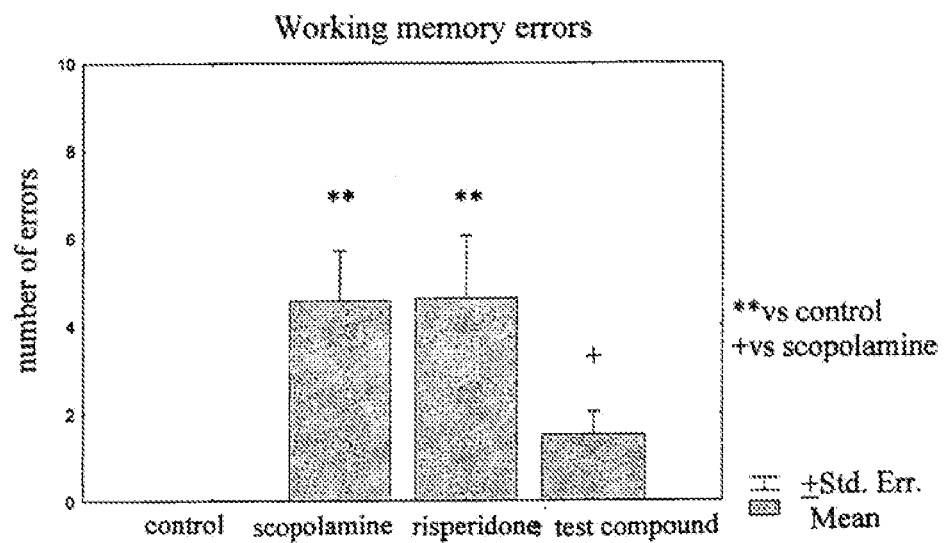
Figure 3:
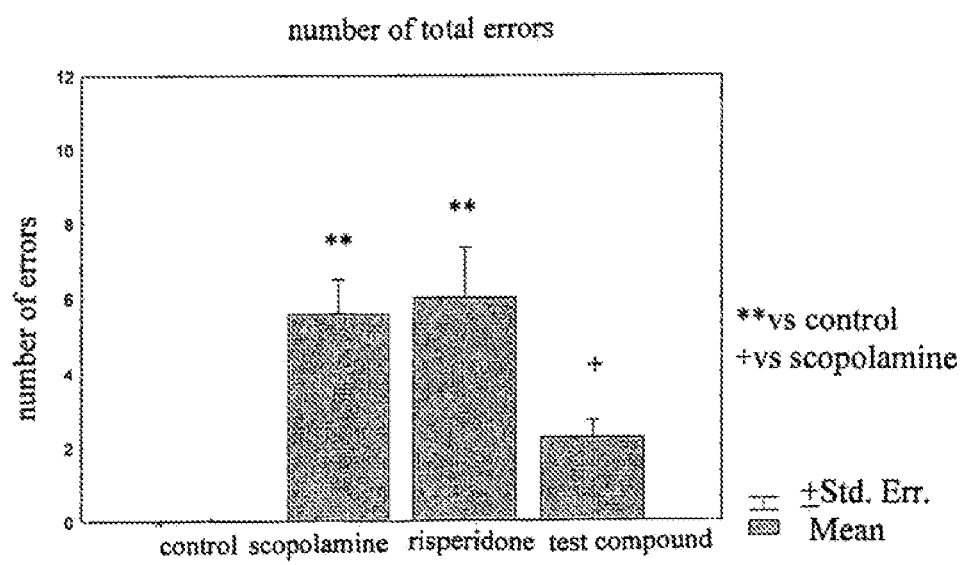
Figure 4:
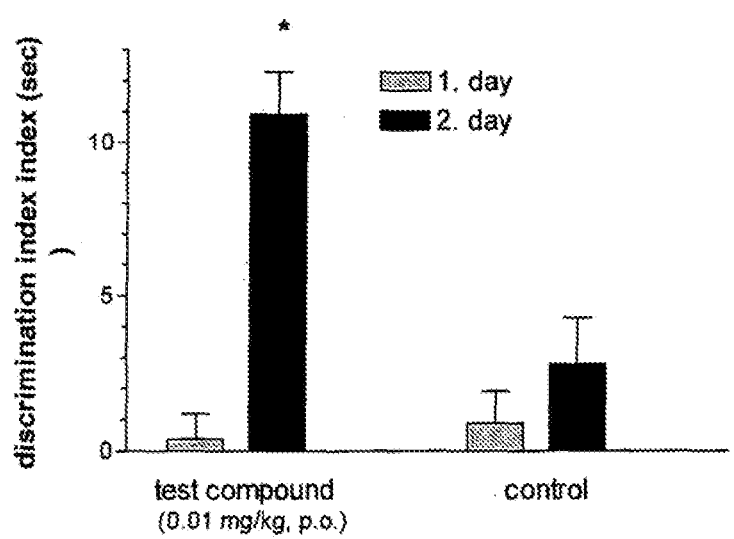
FIG. 4 is a series of bar graphs showing the results of the Object Recognition Test conducted over a two day period in rats following oral administration of 4-chloro-5-{2-[4-(6-fluoro-1,2-benz[d]isoxazole-3-yl)piperidin-1-yl]ethyl-amino}-2-methyl-3-(2H)pyridazinone at a dose of 0.01 mg/kg versus an inert control.

The results are demonstrated in Table 3 and in FIG. 2. On the basis of the test results, it can be concluded that 4-chloro-5-{2-[4-(6-fluoro-1,2-benz[d]isoxazole-3-yl)piperidin-1-yl]ethyl-amino}-2-methyl-3-(2H)pyridazinone of the Formula (I) significantly improved the memory in an extremely low, 0.005 mg/kg dose. In the same dose, risperidone did not exhibit any effect.

TABLE 3

The effects of 4-chloro-5-{2-[4-(6-fluoro-1,2-benz[d]isoxazole-3-yl)piperidin-1-yl]ethyl-amino}-2-methyl-3-(2H) pyridazinone and risperidone in passive avoidance model in rats

| Compound | Dose mg/kg p.o. | Transition latency First Day sec ± SE | No of Cases |
|---|---|---|---|
| Control | — | 22.4 ± 3.9 | 10 |
| 0.4 mA/10 sec electric shock | — | 60.4 ± 11.3** | 8 |
| 0.4 mA/10 sec shock + treatment with 4-chloro-5-{2-[4-(6-fluoro-1,2-benz[d]isoxazole-3-yl)piperidin-1-yl]ethyl-amino}-2-methyl-3-(2H)pyridazinone | 0.005 | 155.9 ± 15.5++ | 9 |
| treatment with 4-chloro-5-{2-[4-(6-fluoro-1,2-benz[d]isoxazole-3-yl)piperidin-1-yl]ethyl-amino}-2-methyl-3-(2H)pyridazinone | 0.005– | 21.2 ± 8.8 | 8 |
| Control | — | 32.4 ± 7.4 | 10 |
| 0.4 mA/10 sec electric shock | — | 92.1 ± 25.0** | 10 |
| 0.4 mA/10 sec electric shock ± risperidone treatment | 0.005 | 85.5 ± 22.0 | 9 |
| Risperidone treatment | 0.005– | 36.1 ± 15.9 | 10 |

**p < 0.05 compared to control
++p < 0.05 compared to 0.4 mA/10 sec electric shock The eight-arm radial maze test is suitable for the study of learning and memory processes and also for the screening of drug candidates influencing such processes.

The apparatus consists of an octagonal central stage (diameter 30 cm, height 25 cm) and eight arms of 70 cm length having 11 cm height attached to the central stage and having their opposite end closed by a feed container. The base of the maze is stainless steel, the walls and the ceiling are made of plexiglass. The feed containers are made of stainless steel.

During the studies, male SPRD rats weighing 240 to 250 g are used. The light-dark cycle of the animals is 12-12 hours, and the light is switched on at 7:00 am. The test were carried out in the light cycle (between 9:00 am and 3:00 pm).

During the so-called dietetic period, the animals are partially fasted, since the famish drive is used for learning. Therefore animals are kept on a diet consisting of 2 piece of standard feed pellet/day for one week. After one week, the body weight of the animals reaches approximately 80 to 85% of that of the normally fed animals.

During the acclimatizing period, the animals are placed in the maze for 10 minutes on the first two days. Each feed container is filled with a small piece of biscuit. Animals are provided with feed after visiting the maze only.

During the learning period, which lasts for 10 to 12 days, the animal should learn to find all pieces of biscuits in the maze and to avoid entering those arms are which have already been visited. After spending five minutes in the maze, the animals are returned into their cages where the daily feed portion is served.

The aim of the selection phase performed after the learning phase is that only those animals would be selected to participate the experiment which have learned the task, i.e. which animal errs maximum once from three trials (TE<=1 and ICR>=7, t<=5 minutes). The movement of the animal was monitored using a video camera, which was set up in the neighboring room.

During the actual testing, the animals were divided into three groups: C (control), S (scopolamine) and T (test). The animals of group C as absolute controls were treated i.p. with a vehicle (0.4% methylcellulose, pre-treatment time 40 minutes) and subcutaneously with solvent (saline, pre-treatment time: 30 minutes). Groups S was treated i.p. with a vehicle and subcutaneously with 0.5 mg/kg scopolamine. The test can be evaluated only in the case when the performance of Groups S is significantly worse than that of group C. Group T was treated intraperitoneally with 0.01 mg/kg dose of 4-chloro-5-{2-[4-(6-fluoro-1,2-benz[d]isoxazole-3-yl)piperidin-1-yl]ethyl-amino}-2-methyl-3-(2H)pyridazinone or 0.01 mg/kg risperidone, respectively and with 0.5 mg/kg dose of scopolamine subcutaneously.

During the testing, the animals were placed in the maze individually, and their movement was monitored using a video camera. When the animals completed their task, they were removed from the maze.

The evaluation of the results comprised the determination of the following variables: number of initial correct answers; number of total errors (TE error); number of arms which were entered multiple occasions (WM error), number of arms which were not entered (RM error), number of arms entered before the first error (ICR). The working memory (WM) error indicates that the working memory of the animal is damaged, since the animal cannot remember the path for entry to a specific arm. The RM error indicates the damage of the reference memory, since the animal cannot recall which arms should be entered (in the present test, all of them).

The statistical evaluation was carried out by variance analysis. The differences between groups were determined by Duncan-test.

On the basis of the test results summarized in Table 4, it can be concluded that 4-chloro-5-{2-[4-(6-fluoro-1,2-benz[d] isoxazole-3-yl)piperidin-1-yl]ethyl-amino}-2-methyl-3-(2H)pyridazinone of the Formula (I) significantly prevented the degradation of memory resulting from scopolamine treatment in all three parameters studied when administered in the dose of 0.01 mg/kg intraperitoneally. In the same dosage, the neuroleptic risperidone did not show a significant effect.

TABLE 4

The effect of 4-chloro-5-{2-[4-(6-fluoro-1,2-benz[d]isoxazole-3-yl)piperidin-1-yl]ethyl-amino}-2-methyl-3-(2H) pyridazinone and risperidone in scopolamine-induced memory deficit in eight-arm maze model in rats

| TREATMENT | DOSE mg/kg | NO. OF cases | ICR (sec) | WME | TE |
|---|---|---|---|---|---|
| Control | — | 7 | 8.0 ± 0 | 0 ± 0 | 0 ± 0 |
| Scopolamine | 0.5 | 7 | 3.4 ± 0.3** | 4.6 ± 1.2** | 5.6 ± 0.9** |
| Risperidone (A-r) | 0.01 | 8 | 3.0 ± 0.1** | 4.2 ± 0.3** | 6.0 ± 0.3** |
| 4-chloro-5-{2-[4-(6-fluoro-1,2-benz[d]isoxazol-3-yl)piperidin-1-yl]ethyl-amino}-2-methyl-3-(2H)pyridazinone (A-t) | 0.01 | 8 | 6.0 ± 0.4**++ | 1.5 ± 0.5+ | 2.3 ± 0.5+ |

**$p < 0.01$ as compared to control
++$p < 0.01$
+$p < 0.05$ as compared to groups S ICR: number of initial correct responses WME: number of working memory errors TE: number of total errors The object recognition test in rats is based on the observation that when animals are encountered with unknown environment, they scour around and discover the available area. They act similarly in case of unknown objects arranged within their area.

In the present experimental arrangement, one day prior to the actual testing day, animals are placed in a box where they have two minutes to get acquainted with the surroundings. On the first day of the experiment, two identical objects (in the present arrangement, a plastic rinse bottle and a glass bottle) are placed in the box and the length of the period is determined during which the animals spend time while examining the two objects. The length of test period is 4-5 minutes. The difference between the length of the time periods spent with the examination of each object is the so-called discrimination index.

On the second day (24 hours after the first testing period) of the experiment, two different objects are placed in the box, among which one is known for the animals and the other is unknown.

In the control group, the discrimination index does not differ significantly, which means that the animals cannot remember the object they became familiar with on the first day. In the case when a memory-enhancing drug is administered to the animals on the first day (e.g. orally, 60 minutes prior to testing), the animals are able to recall the already known objects better and the discrimination index is increased in favour of the unknown object.

It has been found that 4-chloro-5-{2-[4-(6-fluoro-1,2-benz[d]isoxazole-3-yl)piperidin-1-yl]ethyl-amino}-2-methyl-3-(2H)pyridazinone of the Formula (I) significantly enhanced memory functions even in the extremely low dose of 0.01 mg/kg (Table 5).

In summary, the present invention is based on the surprising recognition that 4-chloro-5-{2-[4-(6-fluoro-1,2-benz[d]isoxazole-3-yl)piperidin-1-yl]ethyl-amino}-2-methyl-3-(2H)pyridazinone of the Formula (I) and pharmaceutically acceptable salts thereof possess significant neuroprotective effect, since the compounds are suitable to prevent neuronal death in the CA1 region of the hippocampus resulting from the global cerebral ischemia due to the occlusion of carotid arteries in gerbils and that the compounds significantly decreased the cerebral damage resulting from focal ischemia in rats.

Furthermore, it has been unexpectedly found that 4-chloro-5-{2-[4-(6-fluoro-1,2-benz[d]isoxazole-3-yl)piperidin-1-yl]ethyl-amino}-2-methyl-3-(2H)pyridazinone of the Formula (I) and pharmaceutically acceptable acid addition salts thereof exhibit favourable effect in enhancing learning and memory processes. It has been concluded therefore that 4-chloro-5-{2-[4-(6-fluoro-1,2-benz[d]isoxazole-3-yl)piperidin-1-yl]ethyl-amino}-2-methyl-3-(2H)pyridazinone of the Formula (I) can be advantageously used therapeutically in acute cerebral or spinal neuronal damage of ischemic or traumatic origin, including but not limited to different forms of stroke, cerebral spasms, cerebral vasoconstriction, head or spinal injuries due to an accident, chronic neurodegenerative diseases including motoneuron disease (ALS), multiple sclerosis, Creuzfeld-Jacob disease, Huntington's Disease, Parkinson-disease and in any disease, disorder or state wherein the neurons or a part thereof is damaged or destroyed to decrease the rate of neuronal death and thus decreasing the progression rate of the disease.

Furthermore, 4-chloro-5-{2-[4-(6-fluoro-1,2-benz[d]isoxazole-3-yl)piperidin-1-yl]ethyl-amino}-2-methyl-3-(2H)pyridazinone of the Formula (I) and pharmaceutically acceptable salts thereof are suitable for the treatment and/or

TABLE 5

The effect of 4-chloro-5-{2-[4-(6-fluoro-1,2-benz[d]isoxazol-3-yl)piperidin-1-yl]ethyl-amino}-2-methyl-3-(2H) pyridazinone of the Formula (I) in object recognition model

| Treatment | Dose (mg/kg p.o) | Discrimination index(s) Day 1 | Discrimination index(s) Day 2 | No. Of Cases |
|---|---|---|---|---|
| 4-chloro-5-{2-[4-(6-fluoro-1,2-benz[d]isoxazol-3-yl)-piperidin-1-yl]ethyl-amino}-2-methyl-3-(2H)pyridazinone | 0.01 | 0.4 ± 0.8 | 10.9 ± 1.4* | 14 |
| Control | — | 0.9 ± 1.0 | 2.8 ± 1.5 | 16 |

*$p < 0.05$ as compared to day 1 prevention of diseases, disorders or state wherein the learning or memory functions are damaged or there is a risk of such damage.

Such diseases are Alzheimer's Disease, Korsakoff-disease, Huntington's Disease and Parkinson's Disease together with mental decline due to aging, dementia of cerebrovascular origin or loss of cognitive functions resulting from exposition to toxic substances.

The above-mentioned effect do not follow from the antipsychotic activity of 4-chloro-5-{2-[4-(6-fluoro-1,2-benz[d] isoxazole-3-yl)piperidin-1-yl]ethyl-amino}-2-methyl-3-(2H)pyridazinone of the Formula (I) known from the prior art since the reference compound risperidone of the Formula (II), also has antipsychotic activity, but lacks the above-mentioned neuroprotective and cognition-enhancing effects.

According to the first aspect of the present invention, there is provided a method for the use of 4-chloro-5-{2-[4-(6-fluoro-1,2-benz[d]isoxazole-3-yl)piperidin-1-yl]ethyl-amino}-2-methy 1-3-(2H)pyridazinone of the Formula (I) or a pharmaceutically acceptable salt thereof for obtaining a neuroprotective effect or for influencing the cognitive functions. The use of the compound of the Formula (I) is usually achieved thorough medicaments by administering such medicament containing a therapeutically effective amount of 4-chloro-5-{2-[4-(6-fluoro-1,2-benz[d]isoxazole-3-yl)piperidin-1-yl]ethyl-amino}-2-methyl-3-(2H)pyridazinone or a pharmaceutically acceptable salt thereof to a patient in need of such treatment.

Determination of the actual dose of 4-chloro-5-{2-[4-(6-fluoro-1,2-benz[d]isoxazol-3-yl)piperidin-1-yl]ethyl-amino}-2-methyl-3-(2H)pyridazinone of the Formula (I) or pharmaceutically acceptable salt thereof is the task of a physician.

The usual daily dose of the compound of the Formula (I) is 0.01-300 mg/kg, which depends e.g. on the type, quality and severity of the disease cured, the age, gender, physiological status of the patient, other treatments and the method of administration.

A further aspect of the present invention is the use of 4-chloro-5-{2-[4-(6-fluoro-1,2-benz[d]isoxazole-3-yl)piperidin-1-yl]ethyl-amino}-2-methyl-3-(2H)pyridazinone of the Formula (I) and pharmaceutically acceptable salts thereof for the preparation of a medicament useful for influencing the cognitive function or providing neuroprotective effect.

According to a further aspect of the present invention, there are provided medicaments containing 4-chloro-5-{2-[4-(6-fluoro-1,2-benz[d]isoxazole-3-yl)piperidin-1-yl]ethyl-amino}-2-methyl-3-(2H)pyridazinone of the Formula (I) or a pharmaceutically acceptable salt thereof and a pharmaceutically acceptable vehicle in a mixture optionally with one or more pharmaceutical auxiliary agent known according to the prior art.

The content of the active ingredient in the medicament according to the present invention is usually between 0.1-95 percent by weight, preferably 1 to 50 percent by weight, the most advantageously between 5 and 30 percent by weight.

The medicaments according to the present invention can be administered orally. Oral medicaments can be presented in the form of powders, tablets, coated tablets, chewing tablets, capsules, microcapsules, granules, dragees, lozenges, solutions or emulsions. Another types of the medicaments according to the present invention are suitable for parenteral administration, e.g. injections suitable for intravenous, subcutaneous or intraperitoneal injections or as infusions. Different types of the medicament according to the present invention are to be administered rectally (e.g. suppositories), transdermally (e.g. patches), in the form of implants or locally (e.g. creams, ointments or patches). The solid, semisolid or liquid medicaments according to the present invention can be prepared by the methods known from the prior art.

Medicaments suitable for oral administration according to the present invention contain the active ingredient 4-chloro-5-{2-[4-(6-fluoro-1,2-benz[d]isoxazole-3-yl)piperidin-1-yl]ethyl-amino}-2-methyl-3-(2H)-pyridazinone of the Formula (I) or a pharmaceutically acceptable acid addition salt thereof together with a vehicle or filling agent (e.g. lactose, glucose, starch, calcium phosphate, microcrystalline cellulose), binder (e.g. gelatine, sorbitol, polyvinylpyrrollidone), desintegrant (e.g. croscarmellose, sodium carboxymethyl cellulose, crospovidone), tabletting aids (e.g. magnesium stearate, talc, polyethyleneglycol, silicic acid, silicon dioxide or surfactant (e.g. sodium lauryl sulphate).

Medicaments suitable for oral administration containing 4-chloro-5-{2-[4-(6-fluoro-1,2-benz[d]isoxazole-3-yl)piperidin-1-yl]ethyl-amino}-2-methyl-3-(2H)pyridazinone of the Formula (I) or a pharmaceutically acceptable salt thereof presented in liquid form can be solutions, syrups, suspensions or emulsions and can contain suspending aids (e.g. gelatine, carboxymethyl cellulose), solvents (e.g. water, oils, glycerol, propylene glycol, ethanol), buffers (e.g. acetate, phosphate or citrate buffers) and stabilizing agents (e.g. methyl-4-hydroxy-benzoate).

Parenteral medicaments containing 4-chloro-5-{2-[4-(6-fluoro-1,2-benz[d]isoxazole-3-yl)piperidin-1-yl]ethyl-amino}-2-methyl-3-(2H)pyridazinone of the Formula (I) or a pharmaceutically acceptable salt thereof as active ingredient are sterile isotonic solutions, which can contain besides the solvent buffers and stabilizing agents.

Semisolid medicaments containing 4-chloro-5-{2-[4-(6-fluoro-1,2-benz[d]isoxazol-3-yl)piperidin-1-yl]ethyl-amino}-2-methyl-3-(2H)pyridazinone of the Formula (I) or a pharmaceutically acceptable salt thereof contain the active ingredient homogeneously dispersed in the base of the preparation (e.g. polyethylene glycol, cocoa butter).

The medicaments according to the present invention containing 4-chloro-5-{2-[4-(6-fluoro-1,2-benz[d]isoxazol-3-yl)piperidin-1-yl]ethyl-amino}-2-methyl-3-(2H)pyridazinone or a pharmaceutically acceptable salt thereof can be prepared according to the methods of pharmaceutical technology known from the prior art. The active ingredient is admixed with solid or liquid vehicles and auxiliary agents homogeneously and transformed into a pharmaceutical dosage form. Suitable vehicles and auxiliary materials as well as suitable processes are disclosed in the prior art (Remington's Pharmaceutical Sciences, Edition 18, Mack Publishing Co., Easton, USA, 1990).

Medicaments containing 4-chloro-5-{2-[4-(6-fluoro-1,2-benz[d]isoxazole-3-yl)piperidin-1-yl]ethyl-amino}-2-methyl-3-(2H)pyridazinone of the Formula (I) or a pharmaceutically acceptable salt thereof contain the active ingredient in a unit dosage form.

What We claim is:

1. A method of treating degradation of memory resulting from Alzheimer's disease, cerebrovascular dementia, or acute cerebral damage due to stroke or amnesia in a patient in need of said treatment, which comprises the step of administering to said patient a therapeutically effective amount of 4-chloro-5-{2-[4-(6-fluoro-1,2-benz[d]isoxazole-3-yl)piperidin-1-yl]ethyl-amino}-2-methyl-3-(2H)pyridazinone or a pharmaceutically acceptable salt thereof.

2. A method of treating degradation of memory resulting from Alzheimer's disease, cerebrovascular dementia, acute cerebral damage due to stroke in a patient in need of said treatment, which comprises the step of administering to said patient, a therapeutically effective amount of 4-chloro-5-{2-[4-(6-fluoro-1,2-benz[d]isoxazole-3-yl)piperidin-1-yl]ethyl-amino-2-methyl-3-(2H)pyridazinone or a pharmaceutically acceptable salt thereof.

3. The method of treating the degradation memory defined in claim 2, wherein the patient has Alzheimer's disease.

4. The method of treating the degradation memory defined in claim 2, wherein the patient has cerebrovascular dementia.

5. The method of treating the degradation memory defined in claim 2, wherein the patient has acute cerebral damage due to stroke.

* * * * *